United States Patent
Qiao et al.

(10) Patent No.: US 7,348,147 B2
(45) Date of Patent: *Mar. 25, 2008

(54) METHOD AND SYSTEM FOR NUCLEIC ACID DETECTION

(75) Inventors: Tiecheng A. Qiao, Webster, NY (US); Brian J. Kelley, Farmington, NY (US)

(73) Assignee: Carestream Health, Inc., Rochester, NY (US)

( * ) Notice: Subject to any disclaimer, the term of this patent is extended or adjusted under 35 U.S.C. 154(b) by 443 days.

This patent is subject to a terminal disclaimer.

(21) Appl. No.: 10/989,062

(22) Filed: Nov. 15, 2004

(65) Prior Publication Data

US 2006/0105351 A1    May 18, 2006

(51) Int. Cl.
| | |
|---|---|
| *C12Q 1/68* | (2006.01) |
| *G01N 33/543* | (2006.01) |
| *G01N 33/532* | (2006.01) |
| *G01N 33/53* | (2006.01) |
| *C07C 39/04* | (2006.01) |
| *C09D 189/00* | (2006.01) |

(52) U.S. Cl. .................. 435/6; 436/518; 436/524; 436/527; 436/544; 435/7.1; 435/7.97; 435/7.91; 568/361; 530/812; 106/160.1

(58) Field of Classification Search ................ 436/518, 436/524, 527, 544, 824, 523; 435/7.1, 7.97, 435/6, 7.91, 7.9; 568/362; 530/812; 106/160.1
See application file for complete search history.

(56) References Cited

U.S. PATENT DOCUMENTS

| | | | |
|---|---|---|---|
| 4,782,023 A | 11/1988 | Anawis et al. | |
| 4,962,029 A | 10/1990 | Levenson et al. | |
| 5,182,376 A | 1/1993 | Edwards et al. | |
| 5,650,324 A | 7/1997 | Gorman et al. | |
| 5,776,714 A | 7/1998 | Snoke | |
| 5,792,618 A | 8/1998 | Starkweather et al. | |
| 5,981,180 A | 11/1999 | Chandler et al. | |
| 5,989,842 A | 11/1999 | Schmidt et al. | |
| 6,023,540 A | 2/2000 | Walt et al. | |
| 6,162,610 A | 12/2000 | Bronstein et al. | |
| 6,258,551 B1 * | 7/2001 | Neuenhofer et al. | 435/7.1 |
| 6,815,078 B2 * | 11/2004 | Qiao et al. | 428/478.2 |
| 2003/0068609 A1 | 4/2003 | Chari et al. | |
| 2005/0019828 A1 * | 1/2005 | Qiao et al. | 435/7.1 |
| 2005/0158793 A1 * | 7/2005 | Muraoka et al. | 435/7.1 |

FOREIGN PATENT DOCUMENTS

WO    WO 90/11525    * 10/1990

* cited by examiner

*Primary Examiner*—Long V. Le
*Assistant Examiner*—Shafiqul Haq

(57) ABSTRACT

The present invention relates to a method of detecting nucleic acids comprising suspending at least one recognizable target nucleic acid in a suspending solution containing polymeric particles marked with a probe, wherein the probe has an affinity for the target nucleic acid, adding a recognition unit-peroxidase conjugate marker to the suspending solution, forming a complex of the polymeric particles marked with a probe, the target nucleic acid and the recognition unit-peroxidase conjugate marker, contacting the suspending solution with a gelatin surface, adding a developer to the suspending solution in contact with the gelatin surface in the presence of phenol to attach the complex to the gelatin surface, washing the gelatin surface, and detecting the complex attached to the gelatin surface.

51 Claims, 4 Drawing Sheets

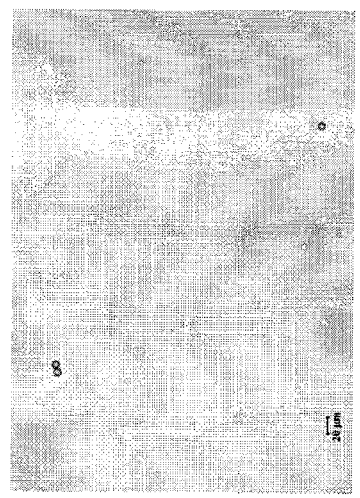
FIG. 4C 5 pM
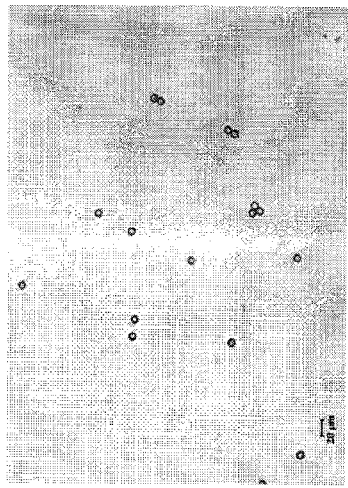
FIG. 4B 0.5 nM
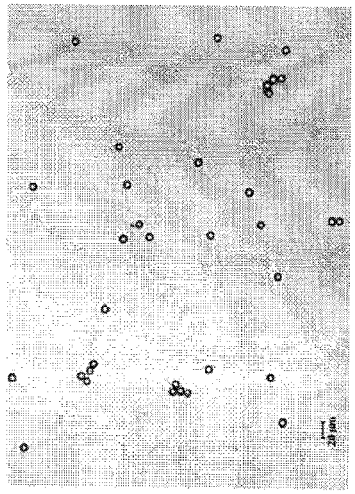
FIG. 4A 50 nM

METHOD AND SYSTEM FOR NUCLEIC ACID DETECTION

CROSS REFERENCE TO RELATED APPLICATIONS

Reference is made to commonly assigned, U.S. Patent Applications:
Ser. No. 10/989,072, now U.S. Pat. No. 7,183,119 by Qiao et al. filed on Nov. 15, 2004 entitled "Method For Sensitive Detection Of Multiple Biological Analytes"; and
Ser. No. 10/988,920, now U.S. Pat. No. 7,074,622 by Qiao et al. filed on Nov. 15, 2004 of entitled "Method And System For Sorting And Separating Particles", the disclosures of which are incorporated herein.

FIELD OF THE INVENTION

The present invention relates generally to the field of methods and devices for detecting nucleic acid molecules and more specifically to methods and devices based on adherence of nucleic acid bound particles to gelatin coated surface.

BACKGROUND OF THE INVENTION

Methods for high-sensitivity detection and characterization of nucleic acid molecules are becoming increasingly important in many fields, such as diagnosis of diseases, early stage detection of a bacterial or viral infection, environmental monitoring, as well as fundamental biological research applications. Most sensitive DNA detection methods utilize the polymerase chain reaction (PCR) to amplify the target DNA sample to increase the concentration of target molecules prior to analysis. To determine the presence of a target DNA molecule, a fluorescently labeled oligonucleotide probe is often used to hybridize to the target DNA sequence and followed by the immobilization of the hybrids to a solid surface. Upon washing off the un-hybridized probes, the fluorescence signal is detected to confirm the presence of target DNA molecule. Alternatively, colormetric labeling can also be used as a means for signal generation. However, these methods are complicated, time-consuming and/or require the use of specialized and expensive equipment. A simple, fast method of detecting nucleic acids which does not require the use of such equipment would clearly be desirable.

PROBLEM TO BE SOLVED

In this invention, we provide a novel approach for the detection of a target DNA molecule utilizing micrometer sized polymeric particles as reporters, which are bound with an oligonucleotide probes of known sequences. When such prepared particles are allowed to interact with a target DNA molecule intended to be identified, the target DNA molecules will bind onto the probes on the surface of the polymeric particles through hybridization between probe sequence and its complementary sequence fragment on the target DNA molecule. The hybrids can be further labeled with a peroxidase which will lead to the adherance of polymeric particle to a gelatin coated surface upon activation by hydrogen peroxide. Therefore the presence of target DNA molecule can be detected.

The international collective effort on whole genome sequencing of various organism has resulted in the deposition of hundred of bacterial and viral genome sequences into gene bank data base. The establishment of such publicly accessible data base make it extremely easy to get access to the whole genome sequence of many disease bacteria and viruses through their accession numbers, for example gram-negative bacterium *Escherichia coli* O157:H7 strain EDL933, as described in the Jan. 25, 2001 issue of Nature (accession number AE005177), and gram-positive bacterium *Bacillus subtilis*, as described in the Nov. 20, 1997 issue of Nature (accession numbers AL009126). Once a bacterium or virus genome sequence is known, it is possible to design multiple gene or DNA probe sequences which are specifically targeted on the unique nucleic acid fragments of the bacterium or virus genome. Such designed gene or DNA probe sequence can be easily made using automatic DNA synthesis machine. This method can be applied, but not limit, to rapid bacterium or virus detection and gene identification.

SUMMARY OF THE INVENTION

The present invention relates to a method of detecting nucleic acids comprising suspending at least one recognizable target nucleic acid in a suspending solution containing polymeric particles marked with a probe, wherein the probe has an affinity for the target nucleic acid, adding a recognition unit-peroxidase conjugate marker to the suspending solution, forming a complex of the polymeric particles marked with a probe, the target nucleic acid and the recognition unit-peroxidase conjugate marker, contacting the suspending solution with a gelatin surface, adding a developer to the suspending solution in contact with the gelatin surface in the presence of phenol to attach the complex to the gelatin surface, washing the gelatin surface, and detecting the complex attached to the gelatin surface.

ADVANTAGEOUS EFFECT OF THE INVENTION

The present invention includes several advantages, not all of which are incorporated in a single embodiment. The present invention provides a method for fast, simple, and inexpensive disease prognosis and diagnosis. The invention is particular useful for detecting DNA from viruses and pathogens.

BRIEF DESCRIPTION OF THE DRAWINGS

FIGS. 4A-4C show microscopic images of detecting target nucleic acid molecules at three different concentrations by attaching particles to gelatin coated surface.

DETAILED DESCRIPTION OF THE INVENTION

Figure 1C:
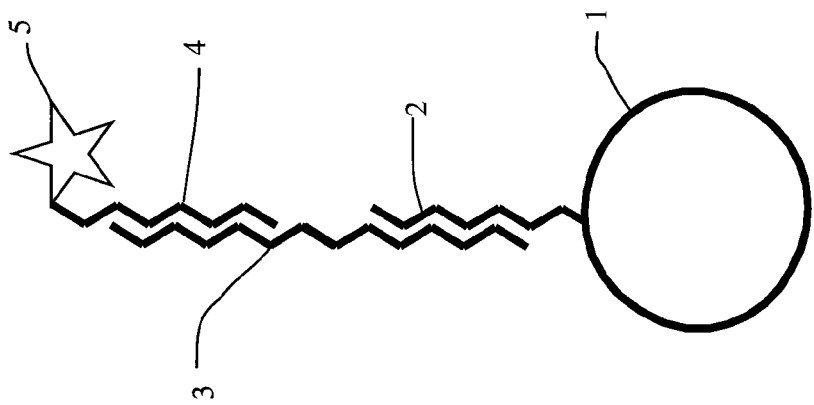
FIGS. 1A-1C are schematic diagrams illustrating the process of a target nucleic acid molecule hybridizing to an oligonucleotide probe modified particle surface followed by the binding of a peroxidase conjugate marker.

The present invention is a novel method for detecting nucleic acid molecules. The method is generally based on the selective immobilization of at least one type of nucleic acid molecule in a mixture of other molecules on a coated surface through a chemical binding process. The nucleic acid molecules to be detected adhere or bind to the surface and become immobilized due to physical or chemical interactions with the surface. The detection method may then be completed by washing the surface to remove any non-adhering (non-immobilized) molecules in the mixture of molecules. As used herein the term "probe" means a molecule or molecular assembly having a strong interaction with a specific target and having a means of being detected following the interaction.

This invention provides a composition and method for selectively detecting nucleic acids that can be specifically recognized by a recognition unit, e.g. an antibody or ligand. It comprises a) a surface coated with gelatin; b) an aqueous solution containing a mixture of marked or identifiable/recognizable nucleic acids suspended; c) a conjugate marker containing a recognition unit and a peroxidase in which the recognition unit has high specific affinity to the marked surface of the nucleic acids to be detected, and d) a polymeric particle marked with a probe having a high affinity to the suspended nucleic acids. The method of detecting nucleic acids comprises 1) suspending a mixture of marked or identifiable/recognizable nucleic acids in an aqueous solution containing polymeric particles marked with a probe having a high affinity to the nucleic acids, 2) adding a recognition unit-peroxidase conjugate marker to the suspension; 3) forming a complex of the polymeric particles marked with a probe, the target nucleic acids and the recognition unit-peroxidase conjugate marker 4) contacting the suspension with a gelatin coated surface; 5) adding a developer to the suspension in contact with the gelatin surface to attach said complex to said gelatin surface; 6) washing the gelatin surface to remove unattached particles and molecules; 7) detecting the complex attached to the gelatin surface. The invention has significant implications for the diagnosis of diseases.

Nucleic acids are biological molecules that carry genetic information. There are two basic kinds of nucleic acids and they are deoxyribonucleic acid (DNA) and ribonucleic acid (RNA). A DNA molecule consists of four nucleotide bases, A, T, G, and C, which are connected in linear manner covalently; and a RNA molecule consists of four bases, A, U, G, and C, which are connected in linear manner covalently. The interaction among four bases follows the "Watson-Crick" base pairing rule of A to T (U) and G to C mediated by hydrogen bonds. When two single strand DNA molecules having a perfect "Watson-Crick" base paring match, they are referred as a complementary strand. The interaction between two complementary strands is termed hybridization.

The nucleic acid to be detected may be isolated by known methods, or may be detected directly in cells, tissue samples, biological fluids (e.g., saliva, urine, blood, serum), solutions containing PCR components, solutions containing large excesses of oligonucleotides or high molecular weight DNA, and other samples, as also known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Methods of preparing nucleic acids for detection with hybridizing probes are well known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). If a nucleic acid is present in small amounts, it may be amplified by methods known in the art. Preferred is polymerase chain reaction (PCR) amplification.

The PCR techniques used for amplifying and thereafter detecting the product are described in detail in U.S. Pat. Nos. 4,683,195 and 4,683,202, the entire disclosures of which are incorporated herein by reference. In general, the PCR amplification process involves an enzymatic chain reaction for preparing, in exponential quantities relative to the number of reaction steps involved, a specific nucleic acid sequence, given that the ends of the required sequence are known in sufficient detail that oligonucleotide primers can be synthesized which will hybridize to them, and that a small amount of the sequence is available to initiate the chain reaction. Specifically, the term "primer" as used herein refers to a molecule comprised of two or more deoxyribonucleotides or ribonucleotides, preferably more than three, which is capable of acting as a point of initiation of synthesis when placed under conditions in which synthesis of a primer extension product which is substantially complementary to a nucleic acid strand is induced, i.e., in the presence of nucleoside triphosphates and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The oligonucleotide primers may be prepared using any suitable automated method with a commercial DNA synthesizer using diethylphosphoramidites as starting materials. The primer must be sufficiently long to prime the synthesis of extension products in the presence of the inducing agent for polymerization. The exact lengths of the primers will depend on many factors, including temperature, buffer, nucleotide composition and source of primer. For purposes herein, the oligonucleotide primer typically contains 15-25 or more nucleotides, although it may contain fewer nucleotides. The primers herein are selected to be "substantially" complementary to each strand of the specific sequence to be amplified. This means that the primers must be sufficiently complementary to hybridize with their respective strands under conditions which allow the agent for polymerization to perform, i.e., the primers have sufficient complementarity with the sequence of the strand to be amplified to hybridize therewith and thereby form a template for synthesis of the extension product of the other primer. Preferably, the primers have exact complementarity with the strand. Typically, these oligonucleotides have different sequences and are complementary to sequences that (1) lie on opposite strands of the template DNA and (2) flank the segment of DNA that is to be amplified. The template DNA is first denatured by heat in the presence of large molar excess of each of the two oligonucleotides and the four dNTPs. The reaction mixture is then cooled to a temperature that allows the oligonucleotide primers to anneal to their target sequences. Afterwards, the annealed primers are extended by the DNA polymerase. The cycle of denaturation, annealing, and DNA-synthesis is then repeated about 10 to 50 times. Since the products of one cycle are used as a template for the next cycle the amount of the amplified DNA fragment is theoretically doubled with each cycle resulting in a PCR-efficiency of 100%. The specific amplification of a target sequence is due to the annealing of the primers to a complementary region of the DNA. If the primer differs in its sequence from the sequence of the annealing region of the target DNA, the PCR may fail. Accordingly, if a target sequence is analyzed that differs between samples in the primer-annealing region, the amplification of the target sequence in some samples will fail or will be less efficient. Therefore, degenerated primers are often used, i.e. primers that have unspecific nucleotide analogous at the positions at which the sequence varies between samples.

If two or more target sequences are amplified simultaneously in the same PCR reaction, a multiplex PCR is performed. Then, more than one primer pair is added to the PCR mixture and each primer pair allows the specific amplification of one target sequence.

The enzyme used for PCR is specific for DNA. If an RNA template is amplified by PCR, the RNA has first to be transcribed into complementary DNA (cDNA) by the enzyme reverse transcriptase. Afterwards the cDNA is used as a template in a PCR. Accordingly, the method of the amplification of RNA is called reverse-transcriptase (Rt) PCR.

The PCR results in a large copy number of the sequence flanked by the primers. The large copy number of this sequence allows the detection and quantification of the target sequence after the PCR reaction. The detection of the amplification products is usually performed by gel electrophoresis and staining of the DNA. The intensity of the band after gel electrophoresis also allows to estimate the copy number of the sequence of interest in the original sample mostly by comparison with a standard with a known copy number (Sambrook et al., *Molecular Cloning*, $2^{nd}$ edition, Cold Spring Harbor Laboratory Press 1989, p. 14.30). The oligo primers for PCR can be pre-labeled with a dye or other marker, e.g. biotin, and such label will be incorporated into the amplified sample.

The particles in this invention can be inorganic or organic particles. The particles can be circular or spherical, square, elliptical, or any other shape. In a preferred embodiment of the invention, the microparticles have a mean diameter of between 1 and 100 microns. Preferably, the mean diameter will be between 2 and 30 microns. Most preferably, the mean diameter will be between 3 and 20 microns. Preferably these particles will be monodisperse or relatively monodisperse. By "monodisperse" it is meant that the coefficient of the particle size distribution (i.e. the standard deviation as a percentage of the mean) will be less than 20%. Preferably, the coefficient of variation will be less than 15%. Most preferably, the coefficient of variation will be less than 10%.

In a preferred embodiment of the invention, polymeric microparticles colored with a dye are used for the invention. However, a polymeric particle such as polystyrene without dye incorporation can be used for the invention as well. The polymeric particles of the invention can be organic or inorganicin composition, having different shapes, such as curvilinear, spherical, donut shaped, elliptical, cubic, rod, etc.

A method for coloring a microparticle has been described by L. B. Bangs in "*Uniform Latex Particles;*" Seragen Diagnostics Inc. 1984, the disclosure of which is hereby incorporated by reference. Another approach to coloring a microparticle with dye is by covalently coupling one or more dyes to the surface of the microparticles. Examples for this approach can be found in U.S. Pat. Nos. 5,194,300 and 4,774,189, the disclosures of which are hereby incorporated by reference. Colorants and pigments can also be incorporated into microparticles using micro-encapsulation methods as described in U.S. Pat. Nos. 5,073,498 and 4,717,655, the disclosures of which are hereby incorporated by reference. These methods can be performed by anyone skilled in the art.

Suitable methods for preparing polymeric particles are emulsion polymerization, as described in "Emulsion Polymerization" by I. Piirma, Academic Press, New York (1982) or by limited coalescence as described by T. H. Whitesides and D. S. Ross in *J. Colloid Interface Science*, vol. 169, pages 48-59, (1985), the disclosures of which are hereby incorporated by reference. The particular polymer employed to make the particles or microparticles is usually a water immiscible synthetic polymer that may be colored, such as any amorphous water immiscible polymer. Examples of polymers that are useful include polystyrene, poly(methyl methacrylate) and poly(butyl acrylate). Copolymers such as a copolymer of styrene and butyl acrylate may also be used.

Once a particle is selected, a probe, which has a high affinity to the target nucleic acids, can be designed and chemically attached to the surface of the particle. For example, a probe has an affinity if it has an affinity binding constant for the nucleic acid of greater than $10^6$ $M^{-1}$. A single-stranded DNA or RNA can be used as a sequence recognition unit to interact with its complementary strand. Sometimes, the complementary strand may contain one or more base-pairing mismatches as well. Some commonly used nucleic acid probes which can used in the invention include, but not limited to, DNA and DNA fragments, RNA and RNA fragment, synthetic oligonucleotides, and peptide nucleic acids.

In another embodiment of the invention, the nucleic acid probe can be any protein scaffold or synthetic molecular moiety capable of recognizing a specific DNA sequence, as described, for example, in U.S. Pat. Appl. Publ. 2003/0170474; 2003/0162181; 2003/0143549, incorporated herein by reference.

A nucleic acid probe can be terminally modified to contain one or more than one chemical functional groups that can be used to attached to another molecule or a surface. Some commonly used terminal modification include, but not limited to, amino, thiol, carboxyl, biotin, and digoxigenin.

The attachment of nucleic acid probe to the surface of microparticles can be performed according to the published procedures in the art (Bangs Laboratories, Inc, Technote #205). Some commonly used chemically reactive groups for the nucleic acid attachment to the particle surface may be, but are not necessarily limited to an aldehyde, epoxy, hydrazide, vinyl sulfone, succinimidyl ester, carbodiimide, maleimide, dithio, iodoacetyl, isocyanate, isothiocyanate, aziridine. Other functionalities which may allow for the attachment of other molecules through the use of a coupling agent or further chemical reactants include primary, secondary, or tertiary amines, thiols, or carboxylic acids. Preferably the reactive unit is a primary or secondary amine, a vinylsulfonyl, or a carboxylic acid. Specific polymers which can be used for this purpose may be selected from the set consisting of, but not necessarily limited to poly (propyleneimine) and polymers and copolymers of N-aminopropyl (meth)acrylamide and secondary amine derivatives thereof, N-aminoethyl (meth)acrylate and secondary amine forms thereof, diallyamine, vinylbenzylamine, vinylamine, (meth) acrylic acid, vinylbenzyl mercaptan, and hydroxyethyl (meth)acrylate. Preferably, the polymer is poly(vinylamine), poly(propyleneimine), or poly(N-aminopropyl methacrylamide), polyacrylic acid, or polymethacrylic acid.

In FIGS. 3A-3D, two different particles 4 and 5 as prepared from the processes of FIG. 1 and FIG. 2. are illustrated as being in contact with the surface 2A of the gelatin layer 2. The particle 4 contains hybrids on its surface with peroxidase conjugate bound to the hybrid, and in contrast the particle 5 represents particles that does not form any hybrids on its surface thus no peroxidase conjugate bound to its surface. The particles 4 and 5 are immersed in or covered with a suitable liquid 3 (it is noted that for the sake of clarity of illustration, only a part of the layer of liquid 3 is illustrated in FIGS. 3A-3D). While the method is schematically illustrated with respect to only two particles 4, and 5, the method may be applied for a plurality of particles (not shown).

The conjugate marker in this invention consists of at least two parts; 1) a recognition unit for the nucleic acid hybrids; 2) a peroxidase enzyme. The recognition unit recognizes the nucleic acid hybrids in a specific manner and binds to the hybrids strongly. Typically the recognition unit should have an affinity constant to the target hybrids of no less than $10^{-6}$ $M^{-1}$. In one preferred embodiment of the invention, a synthetic oligonucleotide is used as recognition units. The oligonucleotide sequence can be the same or different from the nucleic acid probe sequence. In another preferred embodiment of the invention, the recognition unit is a protein such as antibody or antigens. Antibodies are a class of naturally occurring protein molecules that are capable of binding targets with high affinity and specificity. The properties and protocols of using antibody can be found in "*Using Antibodies; A Laboratory Manual*", (Cold Spring Harbor Laboratory Press, by Ed Harlow and David Lane, Cold Spring Harbor, N.Y. 1999). The protein that can be used as recognition units can also be sequence specific DNA or RNA binding proteins, e.g. zinc finger proteins, eucine zipper proteins etc. If a target nucleic acid molecule can be pre-labeled with small molecule marker such as biotin and digoxigenin, then avidin and anti-digoxigenin antibody will be used as recognition unit.

The peroxidase enzyme, can be connected to the recognition unit covalently or non-covalently. The peroxidase-containing conjugate marker used in the practice of the present invention is capable of binding to either the specific binding ligand of interest or its corresponding receptor. The recognition unit may be a labeled analog of the specific binding ligand (such as labeled haptenic derivatives of the ligand). In sandwich assays, the labeled immunoreactant can be a labeled receptor for the ligand, or it can be a labeled molecule (such as a labeled anti-antibody) which binds to the receptor (such as an antibody).

By "peroxidase" in this application is meant any peroxidative substance (enzymatic or otherwise) which catalyzes the oxidation of a substrate, such as a leuco dye, in the presence of hydrogen peroxide or other oxidant to produce an appropriate signal. Microbial, fungal or plant peroxidases are preferred with horseradish peroxidase being most preferred.

The amount of a peroxidase-containing conjugate marker in an element of this invention can vary widely due to the amount of the other components used in the reaction and the suspected amount of particles in the test sample.

The peroxidase-containing conjugate markers useful in this invention is preferably a peroxidase-labeled hapten derivative of the ligand or a peroxidase-labeled antibody. However, a conjugate of avidin or another specific binding compound with peroxidase also can be used in the practice of this invention. Where the label is on a hapten, for example, it can be a peroxidase-labeled drug, hormone, protein, metabolite, chelate or haptenic derivative of any of these. Examples of such materials include, but are not limited to, peroxidase-labeled haptenic derivatives of digoxin, diphenylhydantoin, phenobarbital, C-reactive protein, a thyronine derivative such as thyroxine, carbamazepine or another analyte described above.

The preferred peroxidase for this invention is horseradish peroxidase. Horseradish peroxidase C (E.C.1.11.1.7) (HRP) is the major peroxidase isozyme isolated from the horseradish (Armoracia rusticana). It is a monomeric glycoprotein of 308 amino acids the polypeptide chain having a MW of 33,980 D. There are three neutral carbohydrate side chains and 4 disulphide bridges. The amino acid sequence of the mature protein has been determined. The presence of a pyrrolidonecarboxylyl amino terminus indicates that the protein is probably produced as a precursor form that is processed on secretion. The active form of the enzyme contains a hemin prosthetic group.

The enzyme is particularly stable and is amenable to crosslinking and derivitisation without excessive loss of activity. A further advantage it presents over other enzymatic markers is that some substrates for the enzyme give rise to electron dense products that allow correlation of peroxidase location with cellular ultrastructure using electron microscopy. In addition, horseradish peroxidase is electron dense itself by virtue of the Fe it contains and as a result can act as an E.M. marker in its own right. Particular applications have been found in immunochemistry, where peroxidase cross linked to immunoglobulin is widely used in both ELISA based assay systems and immunocytochemistry. Methods have been described that use either direct crosslinking of peroxidase to the immunoglobulin or indirect crosslinking of biotin labelled immunoglobulin to a streptavidin/horseradish peroxidase complex. Such streptavidin complexes have also found widespread application in nucleic acid hybridzsation methods where biotinylated probe sequences can be localized by sequential incubation with the streptavidin/peroxidase complex and a suitable chromogenic peroxidase substrate. The amino acid sequence of horseradish peroxidase is taught by Welinder, K. G. (Eur. J. Biochem. 96, 483-502 (1979)).

The recognition unit and the peroxidase enzyme can be covalently linked together to form the peroxidase-containing conjugate markers using any of a number of known procedures, and many of such reagents are commercially available from a number of sources. Preparatory procedures include those described by Hermanson in "Bioconjugation Techniques" Academic Press 1996 and in U.S. Pat. No. 5,106,732 (Kondo et al).

Figure 3A:
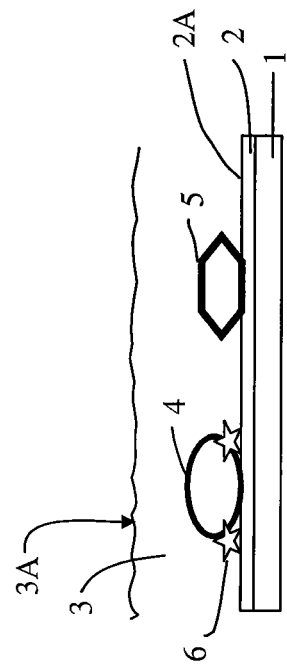
FIGS. 3A-3D are schematic diagrams illustrating the process of selectively attaching peroxidase labeled particles to gelatin coated surface.

The probe-bearing particles may be brought in contact with the surface of the gelatin layer by covering the gelatin layer with an amount of the liquid 3, illustrated in FIG. 3A, in which the particles 4 and 5 are suspended or contained. The said liquid can be buffered aqueous solution or an organic solvent, preferred liquid is a buffer solution. The particles 4 and 5 are allowed to sediment or settle to the surface 2A, either by gravity alone or by centrifugation of the entire support 1 as well as gelatin layer 2, or the slide or vessel or container or other member (not shown) which comprises the support 1 and gelatin layer 2, or by using any other suitable type of method for assisting or accelerating the sedimentation of particles, such as for example, by changing the ionic strength or the pH of the solution in which the particles are suspended by adding suitable salt solutions or buffer solutions, or by using electrophoresis, by attracting the particles to the surface using suitable electrical currents passed between the layer 2 or the substrate 1 and a suitable electrode (not shown) immersed in the liquid 3, or by any other suitable method known in the art for accelerating or assisting the sedimentation of particles.

The suspension can be buffered with one or more typical buffer systems, including but not limited to, phosphate saline buffer, tris buffer, MES buffer, glycine buffer, and acetate buffer.

After the particles are bound with the target nucleic acid as well as the conjugate markers, the suspension containing the particles can be poured over a gelatin coated surface.

Normally, gelatin is coated onto a support and gelation occurs through a process by which gelatin solutions or suspensions of gelatin and other materials form continuous three-dimensional networks that exhibit no steady state flow. This can occur in polymers by polymerization in the presence of polyfunctional monomers, by covalent cross-linking of a dissolved polymer that possesses reactive side chains and by secondary bonding, for example, hydrogen bonding, between polymer molecules in solution. Polymers such as gelatin exhibit thermal gelation which is of the latter type. The process of gelation or setting is characterized by a discontinuous rise in viscosity. (See, P. I. Rose, "The Theory of the Photographic Process", $4^{th}$ Edition, T. H. James ed. pages 51 to 67).

The gelatin substrate described in this invention can either be coated as-is on any solid support, or with one or a combination of multiple hardening agents mixed in the gel. The level of the hardening agent should be from 0 to 20 wt. %, and preferably 0.5 to 8 wt. %, of the total gelatin coated.

There are two types of gelatin: acid pretreated and alkaline pretreated. The preferred gelatin is alkaline pretreated gelatin from bovine bone marrow, but gelatin can also come from other sources. As illustrated in FIG. 3A, the gelatin layer 2 has a surface 2A which is in contact with a fluid or liquid 3 which covers the surface 2A or a portion of the surface 2A. The surface 3A schematically represents the boundary or interface between the liquid 3 and the air or gas overlying the liquid 3.

The gelatin surface for this invention can be flat or slightly curved. The gelatin is coated on a base called the "support" herein. Supports of choice for this invention can be organic, inorganic or biological. Some commonly used support materials include glass, plastics, metals, and semiconductors. The support can be transparent or opaque, flexible or rigid. In some cases, the support can be a porous membrane e.g. nitrocellulose and polyvinylidene difluoride, and the gelatin can be deposited onto the membrane by physical adsorption. The support is preferably made from a transparent substance, such as, but not limited to, glass, quartz, or a suitable plastic material, but other substances or compositions may also be used. However, the material from which the support is made may also be opaque, or partially opaque, depending on the specific implementation or preferred embodiment of the present invention which is being used, and on the particular type of optical system used for implementing the invention, such as but not limited to, in optical systems using epi-illumination or reflected light.

FIG. 3A shows a support 1 coated with a layer of gelatin 2. The support 1 is preferably a flat support, but other types of support, such as but not limited to, curved supports, stepped supports, and other supports having a surface which is not flat or is only partially flat may be used. The support 1 (only a portion of which is illustrated in FIGS. 3A-3D), may be a part of a suitable member, such as but not limited to, a microscope slide (not shown), a Petri dish (not shown), an open container or vessel (not shown), or a covered container or vessel (not shown), or the like, depending on the specific implementation or preferred embodiment of the invention used.

Coating methods are broadly described by Edward Cohen and Edgar B. Gutoff in Chapter 1 of "Modern Coating And Drying Technology", (Interfacial Engineering Series; v.1), (1992), VCH Publishers Inc., New York, N.Y. In general, a fluid coating composition contains a binder, a solvent to dissolve or suspend the components, and optional additives such as surfactants, dispersants, plasticizers, biocides, cross-linking agents for toughness and insolubility, and conductive materials to minimize static buildup. All the components are mixed and dissolved or dispersed, and the coating fluid is sent to an applicator where it is applied to a substrate by one of several coating techniques. Heat is then applied to the coating to evaporate the solvent and produce the desired film, or the coating is solidified by the action of ultraviolet radiation or an electron beam.

The most suitable coating method—including the coating speed—will depend on the quality and functionality desired and the materials being used, e.g., the substrate, the solvent, weight and viscosity of the coating, etc. For a single layer format, suitable coating methods may include dip coating, rod coating, knife coating, blade coating, air knife coating, gravure coating, forward and reverse roll coating, and slot and extrusion coating.

Coating speed can also be an important determinant in the choice of coating method. Although most methods can be used at low speeds, and all methods have a limiting upper speed, some work better at higher speeds. Curtain coating requires a minimum flow to maintain the integrity of the curtain. Therefore, this method is limited to higher speeds if a thin coating is to be obtained. In slide coating of multiple layers, interfacial instabilities are more likely to occur on the slide when the layers are very thin. Higher speeds, with their higher flows and thicker layers on the slide, tend to avoid these instabilities. See, p. 12, "Modern Coating and Drying Technology", supra.

The gelatin has a laydown of 0.2 to 100 grams per square meter; preferably 10 to 50 grams per square meter.

Any well known coating method, such as particle coating or curtain coating, can be used to prepare the gelatin substrate. The gelatin could be coated with any other coating aids such as surfactants and thickeners to adjust its physical property. The gelatin used in the invention may be chemically modified either before, during or after the coating process to create more chemical functionalities that can react or interact with biologically active molecules or assemblies intended to be attached on this substrate.

The developer contains 1) a phenolic compound and 2) hydrogen peroxide. When the developer is added to the suspension solution containing the peroxidase-containing conjugate marker, a substance is formed in the vicinity of the particle 4 by the development. This substance binds or adheres the settled particles which are in contact with the gelatin surface 2A to the gelatin surface. It is believed that this substance is a polyphenolic compound. Thus, the particle 4 adheres to or becomes effectively attached to the gelatin layer 2. In contrast to the particle 4 which becomes attached to the gelatin layer 2, the particle 5 is not attached to the gelatin layer 2 because the region of the layer 2 which underlies the particle 5 does not produce any substance 6.

The developer for this invention can be any hydrogen peroxide containing solution. The developer can be aqueous or non-aqueous, buffered or non-buffered. The concentration of hydrogen peroxide in the developer can be from 0.01% (w/v) to 10% (w/v).

The developer also contains at least one phenolic compound. The phenolic compound may be included in the suspension solution or added to the suspension solution after the suspension is poured over gelatin surface. The phenolic compound may be added in its own solution. The phenol must be added prior to or simultaneously with the hydrogen peroxide.

The phenolic compound is represented by the following general formula:

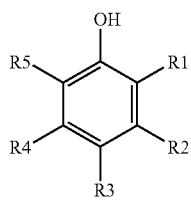

where R1, R2, R3, R4, R5 may be the same or different and may be hydrogen, a substituted or unsubstituted linear or branched alkyl group of 1 to 10 carbon atoms (such as methyl, ethyl, n-propyl, isopropyl, t-butyl, hexyl, decyl, benzyl, methoxymethyl, hydroxyethyl, ethyleneoxy, iso-butyl, and n-butyl), a substituted or unsubstituted aryl group of 6 to 14 carbon atoms (such as phenyl, naphthyl, anthryl, tolyl, xylyl, 3-methoxyphenyl, 4-chlorophenyl, 4-carbomethoxyphenyl and 4-cyanphenyl), a substituted or unsubstituted cycloalkyl group of 5 to 14 carbon atoms such as cyclopentyl, cyclohexyl, and cyclooctyl), a substituted or unsubstituted heterocyclic group (such as pyridyl, pyrimidinyl and furanyl), or a solubilizing group, or a halogen atom of fluoride, chloride, bromide, iodide. Preferably, at least one of the R groups is or contains a solubilizing substituent that is generally negatively charged such as an ionized acidic group. Examples of these solubilizing groups include, but are not limited to, carboxylic acid, sulfonic acid, phosphonic acid, sulfonamide, and hydroxy groups (and their corresponding salts), other solubilizing substituents which may be present on one or more R groups are polyethylenoxy, amino groups and others readily apparent to one skilled in the art. R1 and R2, and R3 and R4, may be joined by sufficient number of carbon, nitrogen, and sulfur atoms to form, independently, a five or six-member ring.

Representative phenolic compounds useful in the present invention are illustrated by the following structures:

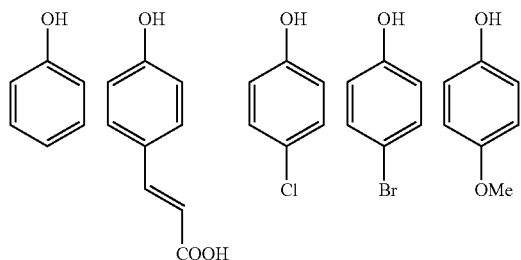

-continued

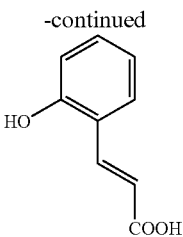

The non-adhered particle 5 may now be removed by suitably washing the gelatin layer 2 with a suitable washing liquid (not shown) applied to the gelatin layer 2 while the adhered particle 4 remains attached to the layer 2. The layer 2 may be washed by additional amounts of a liquid having the same composition as the liquid 3 (preferably without the developer, to minimize the time of exposure of the particles to the developer). Alternatively, the washing may be accomplished by a liquid having a different composition than the liquid 3. The washing step washes the surface 2A of the layer 2, carries away the particle 5 and leaves behind the particle 4 adhered to the layer 2.

Figure 3C:
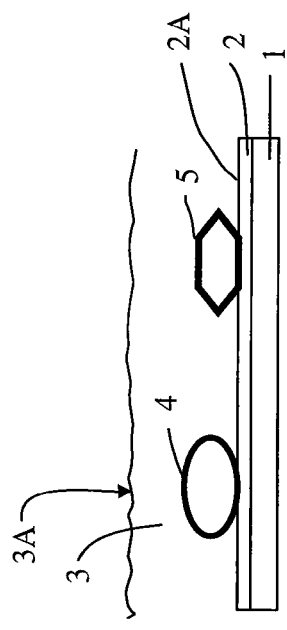
Figure 3B:
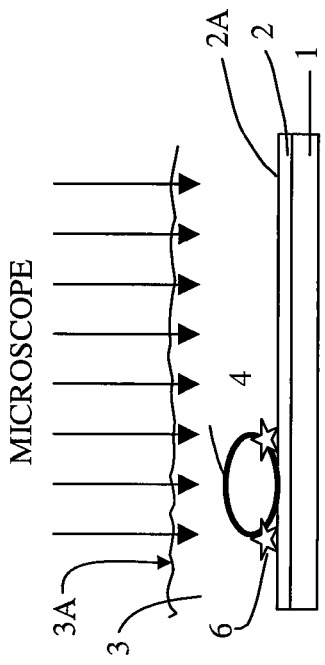

FIG. 3C illustrates the layer 2 and the particle 4 adhering to the gelatin surface 2A after the washing. The particle 5 is not illustrated in FIG. 3C since it has been washed away by the washing step. The washing liquid or fluid (not shown) including the particle 5 (not shown) may be collected for further utilization. Alternatively, the washing fluid may be discarded.

The washing conditions may have to be suitably adapted to ensure a good separation of the particles. Thus, the washing parameters, such as but not limited to, the composition of the washing fluid, the total amount or volume of the washing fluid used, the temperature of the washing fluid, the washing rate or flow rate of the washing fluid (expressed as the volume of washing fluid per time unit), the degree of turbulence in the washing fluid, and other washing parameters, may have to be controlled to ensure that all or most of the non-adhering particles (such as for example the particle 5 of FIG. 3B) will be removed from the gelatin layer 2 in the washing step.

In accordance with one preferred embodiment of the present invention, the identification of the particle may be visually performed. For example, the support may be a part of a microscope slide (not shown in FIGS. 1A-1F), which is visually inspected using an appropriate microscope (not shown), or other suitable microscopy devices. The user of the microscope visually observes the particles and visually identifies the particles. Particles may be differentiated with respect to one or more property, to make them uniquely observable and countable, so that multiple particles may be detected at the same time.

Figure 3D:
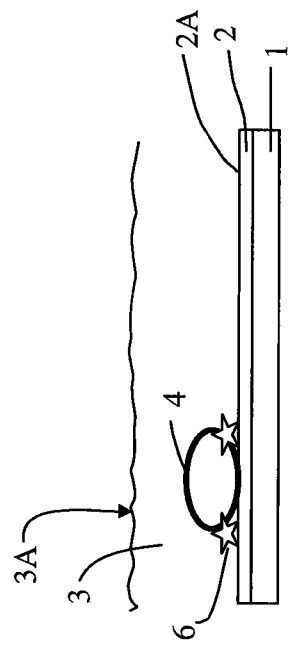

The concentration of target nucleic acid molecule is proportional to the number of particles attached to the gelatin surface, and such number can be quantified by simply counting the number of particle on the surface or by an automatic imaging method to analyze the number of particles on the surface. FIG. 3D shows a possible scheme where particle 4 can be visually detected under a microscope either with the liquid or without the liquid.

It is further noted that, while the optical system or microscope used for implementing some preferred embodiments of the present invention may use trans-illumination of the particles 4 and 5, or of other particles (not shown) which are to be analyzed, other methods of visualization or different methods of illumination may be used for visualizing and identifying the particles to be identified. For example, among the methods and techniques which may be used to visualize and/or identify or distinguish different particles are dark field illumination, epi-illumination, phase-contrast microscopy, differential interference contrast microscopy (DIC), polarization microscopy, multi-spectral or hyper-spectral microscopy involving the acquisition and analysis of pixel level spectrogram data as is known in the art, and any other suitable microscopy methods known in the art which may be adapted for use with the methods of the present invention.

Preferably, overlap of the particles should be avoided by proper adjustment of number of the particles to avoid or minimize the adhering of the "wrong" particles to the gelatin surface. The number of the particles is preferably optimized to avoid such undesirable adhering of particles. However, the particle number should be sufficiently high to allow the practical identification of the particles. Thus, the actual initial number of particles in the fluid suspension applied to the gelatin layer 2 may be a compromise which practically avoids contaminating undesired particles, while still ensuring high yield of the required particles to be identified. The initial number particles may also depend on the type and morphological parameters of the particles, and on other factors. For certain applications in which a single particle, or very few particles is sufficient, a very low initial number of particles may be utilized in implementing the method of the present invention.

Figure 1B:
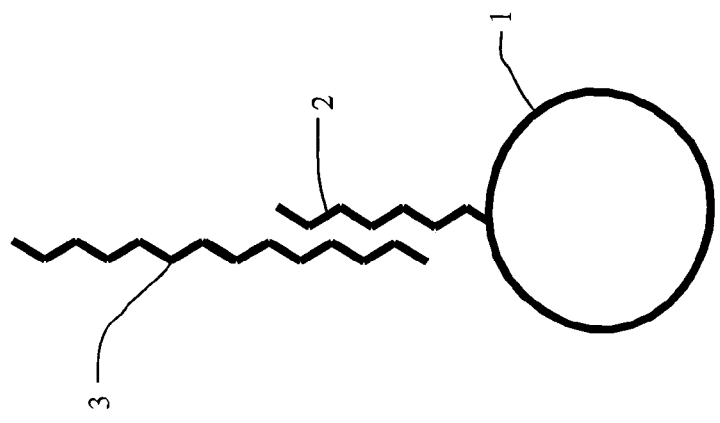
Figure 1A:
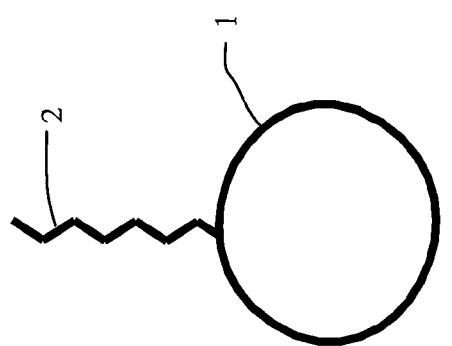
Figure 2A:
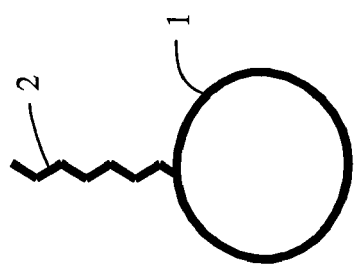
FIGS. 2A-2D are schematic diagrams illustrating the process of a PCR amplified target nucleic acid molecule labeled with biotin hybridizing to an oligonucleotide probe modified particle surface followed by the binding of a peroxidase-avidin conjugate marker.
Figure 2B:
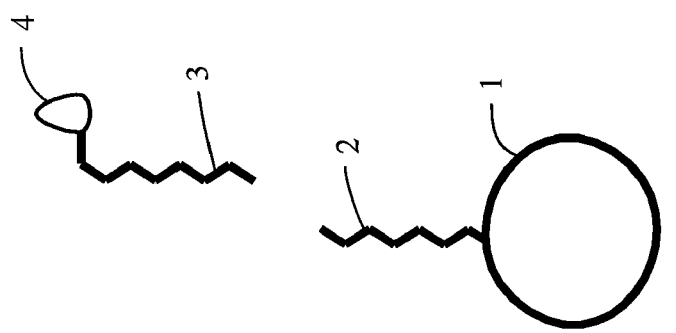
Figure 2C:
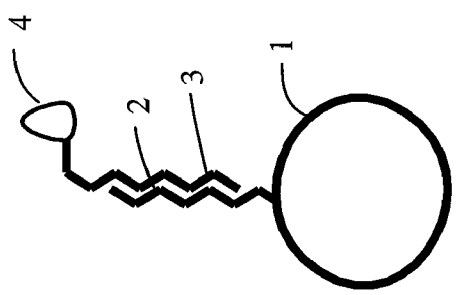
Figure 2D:
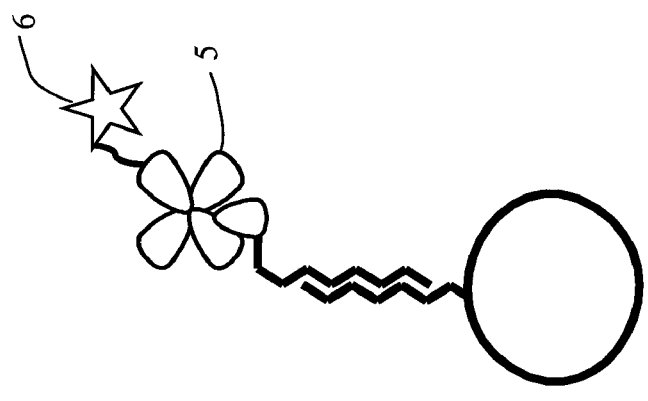

The invention is now described in reference to FIGS. 1-3, which are schematic diagrams illustrating the nucleic acid detection method of the invention in accordance with one preferred embodiment of the present invention. FIG. 1A shows schematically one preferred embodiment of the invention in which a particle 1 is modified on its surface with an oligonucleotide probe 2. Only one oligonucleotide probe is shown in the figure, but more than one probe can be attached to the surface of the particle. In FIG. 1B, a target nucleic acid molecule 3 to be identified is hybridized to probe 2 through interaction of their respective complementary sequences to form a hybrid on the surface of the particle 1. In FIG. 1C a conjugate marker consisting of an oligonucleotide probe 4 and peroxidase 5 is hybridized to target nucleic acid molecule 3 through interaction of their respective complementary sequences. The particles consisting of hybrid structure on their surfaces as shown in FIG. 1C are now ready to be spread onto a gelatin surface. FIG. 2A shows schematically another preferred embodiment of the invention in which a particle 1 is modified on its surface with an oligonucleotide probe 2. Only one oligonucleotide probe is shown in the figure, but more than one probe can be attached to the surface of the particle. FIG. 2B shows schematically addition of a PCR amplified target consisting of target nucleic acid fragment 3 and a biotin label 4 to particle 1 with probe 2. In FIG. 2C the PCR product is hybrized to probe 2 through interaction of their respective complementary sequences. A conjugate marker consisting of avidin 5 and peroxidase 6 is added in FIG. 2D to bind to the biotinylated hybrid. The particles consisting of hybrid structure on their surfaces as shown in FIG. 2D are now ready to be spreaded onto a gelatin surface. The process of spreading and adherence of particles shown in FIGS. 1C and 2D is schematically shown in FIG. 3A-D.

The invention can be better appreciated by reference to the following specific embodiments.

EXAMPLES

Preparation of Gelatin Coating

Solution A: 147.8 g of 35% gelatin solution, 963 g of water, 46.8 g of 9% siloxanes & silicones, di-Me, 2.5 g of 4.97% 1H-1,2,4-Triazolium, 1,4-diphnyl-3-(phenylamino)-inner salt, 3.55 g of 7.6% 2,4-Pentanediol, 2-methyl, and 36 g of 6.68% Ethanesulfonic acid, 2(2-(2-(4-(1,1,3,3-tetramethyl butyl) phenoxy)ethoxy)ethoxy)-, sodium salt.

Solution B: 106.2 g of 1.79% 1,1'-(methylene bis(sulfonyl) bis-ethene and 1,094 g of water.

Solution A and solution B were coated at 29.71 mL/square meter and 15.01 mL/square meter, respectively. The two solutions were delivered to and mixed at the coating hopper. The resulting coating was then dried. The coating contained 1.399 g of gelatin/square meter.

Preparation of DNA Modified Particles:

Spin down 500 μL of 10 μM colored carboxy modified polystyrene particles (1% w/w) in a 1.5 mL eppendorf tube for 3 minutes at 13000 RPM. Carefully remove supernatant and add 1 mL of 0.05 M acetate buffer, with 0.05% (w/w) Tween 20 pH 5.0, vortex to homogenize. Repeat acetate buffer wash a second time and remove supernatant. Add 1 mL of the following solution: 0.1 M N-hydroxysuccinimide, (NHS) and 0.05 M 1-[3(dimethylamino)propyl]-3-ethylcarbodiimide hydrochloride (EDC) dissolved in 0.05 M acetate buffer (115 mg NHS, 96 mg EDC, 10 mL acetate buffer). Vortex to homogenize and react for 1 hour at room temperature with agitation. Spin down particles for three minutes at 13000 RPM, remove supernatant and wash with acetate buffer, removing supernatant. In a separate tube combine 100 μL polyethyleneimine (MW 1200) (PEI) and 900 μL of acetate buffer in a tube, mix well, add to particle pellet. React for 1 hour at room temperature. Wash particles two times in PBS buffer with 0.05% Tween 20 pH 7.4, remove supernatant. To 100 μL of 1 nmol of oligmer DNA (5'-/5AmMC6/AGG TGA ACG TGG ATG AAG TT-3') in distilled water add 100 μL of (1 mg/mL) cyanuric chloride in acetonitrile. Add 300 μL 0.1 M boric acid pH 8.3 buffer. React for one hour at room temperature with agitation. Dialyze twice through a 3,500 MW cutoff membrane in 1L of 0.1 M Boric Acid, pH 8.3 buffer for 1.5 hours each time. Combine dialyzed DNA with PEI modified particles dissolved in 500 μL 0.1 M Boric Acid pH 8.3 buffer. React for 1 hour at room temperature with agitation. Wash two times in PBS buffer with 0.05% Tween 20, pH 7.4. Re-suspend in 500 μL of PBS buffer with 0.05% Tween 20.

DNA Hybridization and Particle Attachment

Invention: To three 10 μL of 1% particles that have been modified with PEI and DNA add 490 μL of 6×SSPE-SDS buffer and three different concentrations—50 nM, 0.5 nM, and 5 pM, of target nucleic acid sample with 5' biotin labeling (5'-/5Bio/AAC TTC ATC CAC GTT CAC GTT CAC CT-3') are added. Mix well. Immerse tube in 700 mL of 70° C. water and allow to cool to room temperature and then place tubes in an ice bath for 10 min. Spin down tubes and remove supernatant. Wash two times with 0.5×SSPE-SDS buffer. Suspend particles in a 0.01 mg/mL solution of avidin-horseradish peroxidase in PBS buffer with 0.05% Tween 20. Incubate with agitation for 1 hour at room temperature. Wash three times with PBS buffer with 0.05% Tween 20. Re-suspend in 90 uL of 0.05M tris buffer pH 8.5 with 0.75 mg/mL p-coumaric acid. Apply solution to a 25 mm×76 mm piece of gelatin coated substrate. Wait five minutes and add 15 μL of 0.4% hydrogen peroxide in water.

Wait five minutes and wash coating by pouring approximately 100 mL of distilled water over it. Observe under a microscope (100× magnification). More than 95% of particles are attached to the coating that indicates the detection of target analytes. The relative number of the particles attached to the gelatin surface are shown in FIG. 4A-4C with the same magnification.

Control:

To 10 µL of 1% particles that have been modified with PEI and DNA add 490 µL of 6×SSPE-SDS buffer. Mix well. Immerse tube in 700 mL of 70 C water and allow to cool to room temperature and then place tubes in an ice bath for 10 min. Spin down tubes and remove supernatant. Wash two times with 0.5×SSPE-SDS buffer. Suspend particles in a 0.01 mg/mL solution of avidin-horseradish peroxidase in PBS buffer with 0.05% Tween 20. Incubate with agitation for 1 hour at room temperature. Wash three times with PBS buffer with 0.05% Tween 20. Re-suspend in 90 µL of 0.05M tris buffer pH 8.5 with 0.75 mg/mL p-coumaric acid. Apply solution to a 25 mm×76 mm piece of gelatin coated substrate. Wait five minutes and add 15 µL of 0.4% hydrogen peroxide in water. Wait five minutes and wash coating by pouring approximately 100 mL of distilled water over it. Observe under a microscope (100× magnification). Less than 0.01% of particles are attached to the coating that indicates the absence of target analytes.

The invention has been described in detail with particular reference to certain preferred embodiments thereof, but it will be understood that variations and modifications can be effected within the spirit and scope of the invention.

The invention claimed is:

1. A method of detecting nucleic acids comprising:
   suspending at least one target nucleic acid in a suspending solution containing polymeric particles attached to a probe, wherein said probe has specific affinity for said target nucleic acid;
   adding a recognition unit-peroxidase conjugate marker to said suspending solution, wherein the recognition-unit peroxidase conjugate associates with said target nucleic acid;
   forming a complex of said polymeric particles attached to a probe, said target nucleic acid and said recognition unit-peroxidase conjugate marker in said suspending solution;
   contacting the suspending solution containing said complex with a gelatin surface;
   adding a developer comprising hydrogen peroxide to said suspending solution containing said complex in contact with said gelatin surface in the presence of phenol to attach said complex to said gelatin surface;
   washing said gelatin surface; and
   detecting said complex attached to said gelatin surface.

2. The method of claim 1 wherein said target nucleic acid is deoxyribonucleic acid (DNA) or ribonucleic acid (RNA).

3. The method of claim 1 wherein said nucleic acid is amplified by polymerase chain reaction (PCR) amplification.

4. The method of claim 1 wherein said suspending solution is an aqueous solution.

5. The method of claim 4 wherein said suspending solution is buffered.

6. The method of claim 1 wherein said suspending solution further comprises phenol.

7. The method of claim 1 wherein said polymeric particles are organic.

8. The method of claim 1 wherein said polymeric particles are inorganic.

9. The method of claim 1 wherein said polymeric particles have a distinct color, shape or size.

10. The method of claim 9 wherein said shape is curvilinear, spherical, donut shaped, elliptical, cubic, or rod.

11. The method of claim 9 wherein said color is derived from mixing three dyes representing the primary colors R, G, B to create distinct "color addresses."

12. The method of claim 11 wherein each of said distinct "color addresses" corresponds to a specific bioactive probe.

13. The method of claim 9 wherein said color is derived by covalently coupling one or more dyes to the surface of said polymeric particles.

14. The method of claim 9 wherein said color is derived from micro-encapsulated colorants and pigments incorporated into said polymeric particles.

15. The method of claim 1 wherein said polymeric particles are polystyrene, poly(methyl methacrylate) and poly(butyl acrylate).

16. The method of claim 1 wherein said polymeric particles have a mean diameter of from 1 to 100 microns.

17. The method of claim 1 wherein said polymeric particles have a mean diameter of from 2 to 30 microns.

18. The method of claim 1 wherein said polymeric particles have a mean diameter of from 3 to 20 microns.

19. The method of claim 1 wherein said polymeric particles are monodisperse wherein the coefficient of the particle size distribution (i.e. the standard deviation as a percentage of the mean) will be less than 20%.

20. The method of claim 1 wherein said polymeric particles are a plurality of particles types, wherein each type of particle is distinguishable from each other type of particle.

21. The method of claim 1 wherein said probe is a DNA or DNA fragments, RNA or RNA fragment, synthetic oligonucleotide, or peptide nucleic acid.

22. The method of claim 21 wherein said probe has an affinity binding constant to said target nucleic acid of greater than $10^6$ $M^{-1}$.

23. The method of claim 22 wherein said probe is a protein scaffold or synthetic molecular moiety capable of recognizing a specific DNA sequence.

24. The method of claim 1 wherein said probe is an antigen.

25. The method of claim 1 wherein said recognition unit is an antibody.

26. The method of claim 1 wherein said recognition unit has an affinity binding constant to the target nucleic acid of no less than $10^{-6}$ $M^{-1}$.

27. The method of claim 1 wherein said recognition unit is the same as said probe.

28. The method of claim 1 wherein said recognition unit is a synthetic oligonucleotide.

29. The method of claim 1 wherein said peroxidase is connected to the recognition unit covalently.

30. The method of claim 1 wherein said peroxidase is connected to the recognition unit non-covalently.

31. The method of claim 1 wherein said peroxidase is horseradish peroxidase (HRP).

32. The method of claim 1 wherein said gelatin is coated onto a support.

33. The method of claim 32 wherein said support is organic, inorganic or biological.

34. The method of claim 32 wherein said support is glass, quartz, plastics, metals, semiconductors, a porous membrane.

35. The method of claim 1 wherein said gelatin further comprises hardener.

36. The method of claim 1 wherein said gelatin has a lay down of from 0.2 to 100 grams per square meter.

37. The method of claim 1 wherein said gelatin has a lay down of from 10 to 50 grams per square meter.

38. The method of claim 1 wherein the concentration of said hydrogen peroxide in said developer is from 0.01% (w/v) to 10% (w/v).

39. The method of claim 1 wherein said developer is aqueous.

40. The method of claim 1 wherein said developer is buffered.

41. The method of claim 1 wherein said developer further contains phenol.

42. The method of claim 1 wherein said phenol is added prior to or simultaneously with said developer.

43. The method of claim 1 wherein said phenol is represented by the following general formula:

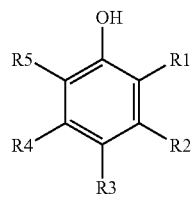

where R1, R2, R3, R4, R5 are independently a hydrogen, a substituted or unsubstituted linear or branched alkyl group of 1 to 10 carbon atoms, a substituted or unsubstituted aryl group of 6 to 14 carbon atoms, a substituted or unsubstituted cycloalkyl group of 5 to 14 carbon atoms, a substituted or unsubstituted heterocyclic group, a solubilizing group, or a halogen atom of fluoride, chloride, bromide, iodide.

44. The method of claim 43 wherein at least one of R1, R2, R3, R4, R5 is or contains a solubilizing substituent that is generally negatively charged.

45. The method of claim 1 wherein said phenol is represented by at least one of the following structures:

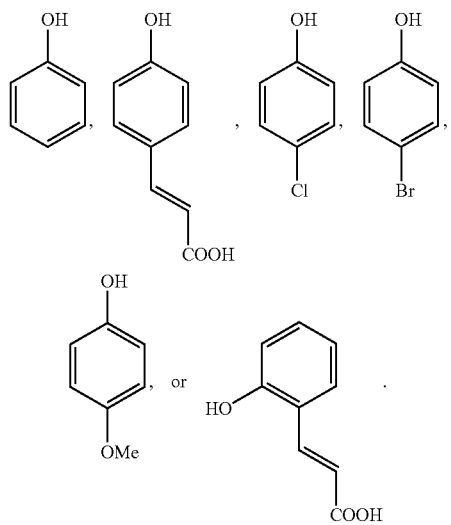

46. The method of claim 1 wherein said washing is aqueous.

47. The method of claim 1 wherein said detecting is visual inspecting.

48. The method of claim 47 wherein said visual inspecting utilizes a microscope.

49. The method of claim 1 wherein said detecting is automatic imaging.

50. The method of claim 1 wherein said detecting is dark field illumination, epi-illumination, phase-contrast microscopy, differential interference contrast microscopy (DIC), polarization microscopy, multi-spectral or hyper-spectral microscopy.

51. The method of claim 1 wherein said detecting is full-frame image capture.

* * * * *